United States Patent [19]

Reineke

[11] 4,321,193

[45] Mar. 23, 1982

[54] PREPARATION OF N-HALO α,α-DISUBSTITUTED β-LACTAMS

[75] Inventor: Charles E. Reineke, Midland, Mich.

[73] Assignee: The Dow Chemical Company, Midland, Mich.

[21] Appl. No.: 870,311

[22] Filed: Jan. 18, 1978

[51] Int. Cl.$^3$ .......................................... C07D 205/08
[52] U.S. Cl. ................................................ 260/239 A
[58] Field of Search ................................. 260/239 AL

[56] References Cited

U.S. PATENT DOCUMENTS 3,297,754  1/1967  Bantjes .......................... 260/239 AL
3,711,469  1/1973  Merger .......................... 260/239 AL
3,775,468  11/1973  Kampe .......................... 260/239 AL

OTHER PUBLICATIONS

E. S. Wallis, "Organic Reactions", vol. III, Chapter 7, pp. 267–286.
Kent, "Organic Synthesis" Collective vol. III, pp. 490–492.
F. Nerdel, Chem. Ber. 91, pp. 938–943 (1958).
Djerass; Chem. Reviews 43, 271 (1948).
Taub et al., J. Org. Chem. 25, pp. 263–264 (1960).

*Primary Examiner*—Mark L. Berch

[57] ABSTRACT

A process for preparing N-halo α,α-disubstituted β-lactams comprising reacting a 3-halo 2,2-bis(halomethyl) propionamide with a sufficient amount of an aqueous solution of a hypohalite to form the corresponding N-halo 3,3-bis-(halomethyl)-2-azetidinone.

3 Claims, No Drawings

PREPARATION OF N-HALO α,α-DISUBSTITUTED β-LACTAMS

BACKGROUND OF THE INVENTION

The present invention relates to a process for preparing β-lactams (2-azetidinones), and more in particular to a process for preparing N-halo α,α-disubstituted β-lactams.

β-Lactams, which are the inner cyclic amides of β-amino acids, are generally made by the action of a Grignard reagent upon β-aminopropionic esters, or by the action of a base upon β-aminopropionic acid chlorides. β-Lactams bearing chloromethyl substituents on the α-carbon atom and hydrogen on the amido nitrogen atom are prepared by treating an α,α-disubstituted β-halopropionic acid amide with selected alkali or alkaline earth metal salts of weakly acidic compounds. This method is described in U.S. Pat. No. 3,297,754.

Amides are known to react with aqueous hypohalite solution to form the corresponding amine by the Hoffman reaction. This reaction is described in more detail by E. S. Wallis in "Organic Reactions", Vol. III, Chap. 7, pp. 267–286.

SUMMARY OF THE INVENTION

A process has now been discovered for preparing N-halo α,α-disubstituted β-lactams. The process comprises reacting a 3-halo 2,2-bis(halomethyl)propionamide with an aqueous solution of a hypohalite.

It was unexpected that an N-halo β-lactam could be prepared from 3-halo 2,2-bis(halomethyl)propionamide by the present process, because the reaction of an aqueous hypohalite solution with an amide normally forms the corresponding amine by the Hoffman reaction cited above. In contrast, the instant process produces very little, if any, of the amine.

N-halo β-lactams produced by the present process are useful as intermediates in forming β-lactams which can be polymerized to form polyamide compositions. These compositions exhibit excellent properties as intumescent and flame retardant additives in various coating formulations. The intumescent flame retardant polyamides are described in a commonly owned co-pending U.S. patent application, Ser. No. 870,312, filed Jan. 18, 1978, for "Flame Retardant Intumescent Polyamides". That application is incorporated herein by reference. The formation of β-lactams from the intermediate N-halo β-lactams is described in a commonly owned co-pending U.S. patent application, Ser. No. 870,407, filed Jan. 18, 1978, for "α,α-Disubstituted β-Lactams". That application is incorporated herein by reference.

DETAILED DESCRIPTION OF THE INVENTION

Propionamides suitable for use as starting materials in the practice of the present process, are 3-halo 2,2-bis(halomethyl)propionamides of the formula I.

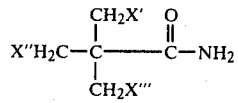

where X', X" and X'" are independently bromo or chloro. Specific examples of compounds falling within formula I are: 3-chloro 2,2-bis(chloromethyl)propionamide; 3-chloro 2-chloromethyl-2-bromomethylpropionamide; 3-chloro 2,2-bis(bromomethyl)propionamide; 3-bromo 2,2-bis(chloromethyl)propionamide; 3-bromo 2-chloromethyl-2-bromomethylpropionamide; and 3-bromo 2,2-bis(bromomethyl)propionamide. Such compounds are well known and can be conveniently prepared by converting the β-halo acid to the acid halide with thionyl halide or phosphorus halide. The resulting acid halide is then reacted with aqueous ammonia in a manner similar to that described in "Organic Syntheses", Collective Manual III, pp. 490–492. A similar technique for preparing the propionamides is described by F. Nerdel, A. Heymons, H. Croon, in *Chemische Berichte*, 91, pp. 938–943 (1958).

The propionamides of formula I are allowed to react with a sufficient amount of an aqueous solution of a hypohalite to form the corresponding N-halo 3,3-bis(halomethyl)-2-azetidinone of formula II

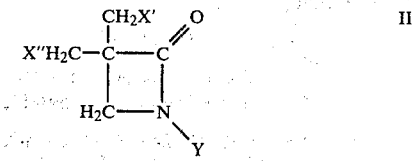

where X', X", and Y are each independently bromo or chloro. Specific examples of N-halo azetidinones falling within formula II are: N-chloro 3,3-bis(chloromethyl)-2-azetidinone; N-chloro 3-(bromomethyl)-3-(chloromethyl)-2-azetidinone; N-chloro 3,3-bis(bromomethyl)-2-azetidinone; N-bromo 3,3-bis(chloromethyl)-2-azetidinone; N-bromo 3-(bromomethyl)-3-(chloromethyl)-2-azetidinone; and N-bromo 3,3-bis(bromomethyl)-2-azetidinone.

The instant process is illustrated by the following equation where aqueous sodium hypobromite is allowed to react with 3-bromo 2,2-bis(bromomethyl)propionamide:

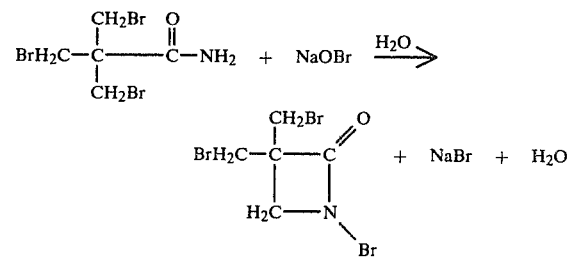

Suitable hypohalite compounds which can be used are those which effect displacement of a halogen from the α-halomethyl group and effect cyclization of the propionamides to the β-lactam ring. Such hypohalite compounds include, for example, the alkali metal and alkaline earth metal hypochlorites and hypobromites. Sodium hyprobromite, sodium hyprochlorite, or mixtures thereof are preferred because of their commercial availability.

The hypohalite is preferably formed prior to contacting the propionamide by allowing a halogen to react with an alkali metal base or an alkaline earth metal base. Alkali metal and alkaline earth metal hydroxides, bicarbonates, mixtures thereof, and the like are suitable bases in this reaction. Representative of such bases are sodium hydroxide, potassium hydroxide, magnesium hydroxide, calcium hydroxide, sodium bicarbonate, potassium bicarbonate, magnesium carbonate, calcium carbonate, and the like. Suitable halogens include bromine, chlorine, bromine chloride, and mixtures thereof. Preferably, a stoichiometric excess of the halogen and base are used because the reaction of these materials in forming the hypohalite is normally less than quantitative. A mole ratio of halogen/base of about 1/2.5 has been satisfactory in most instances.

The reaction of the propionamide with the aqueous hypohalite solution is normally conducted at a temperature sufficient to effect cyclization of the propionamides while avoiding halogen hydrolysis side reactions. A reaction temperature of from about $-10°$ C. to about $50°$ C. is normally used. However, a reaction temperature of from about $0°$ C. to about $25°$ C. is preferred and a temperature of from about $0°$ C. to about $10°$ C. is more preferred.

The invention is further illustrated by the following example:

EXAMPLE

Preparation of N-bromo 3,3-bis(bromomethyl)-2-azetidinone

A sodium hypobromite solution was prepared by adding 1.8 milliliters (ml) (0.036 mole) of bromine to a solution of 7.2 grams (g) (0.18 mole) of sodium hydroxide in 60 ml of water. The resulting solution was stirred at about $4°-10°$ C. while 1.0 g (0.030 mole) of 3-bromo 2,2-bis-(bromomethyl)propionamide was added in one portion. The stirring was continued for another 60 minutes. An insoluble white solid product formed during the stirring. The solid product was collected by filtration and dried in vacuo. After drying, 6.3 g of the solid were obtained. The solid melted at $60°-64°$ C., and was found by elemental analysis and iodometric titration to be N-bromo 3,3-bis-(bromomethyl)-2-azetidinone. The iodometric titration of the solid showed an active bromine content of about 24.0 percent by weight. The theoretical active bromine content of N-bromo 3,3-bis(-bromomethyl)-2-azetidinone is 23.8 percent by weight.

What is claimed is:

1. A process of producing an N-halo $\alpha,\alpha$-disubstituted $\beta$-lactam of the formula:

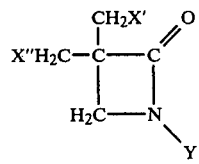

where X', X" and Y are each independently bromo or chloro comprising reacting a 3-halo 2,2-bis(halomethyl) propionamide with an aqueous solution of a hypohalite.

2. The process of claim 1 wherein the hypohalite is selected from the group consisting of an alkali metal hypochlorite, an alkaline earth metal hypochlorite, an alkali metal hyprobromite, and an alkaline earth metal hypobromite, or a mixture thereof.

3. The process of claim 1 wherein the reaction is conducted at a temperature of from about $-10°$ to about $50°$ C.

* * * * *